United States Patent
Ren et al.

(10) Patent No.: US 11,659,791 B2
(45) Date of Patent: May 30, 2023

(54) RHIZOME-GROWTH MONITORING DEVICE OF CLONAL PLATE IN SHIFTING DUNE

(71) Applicant: Northwest Institute of Eco-Environment and Resources, CAS, Lanzhou (CN)

(72) Inventors: Heng Ren, Lanzhou (CN); Wenzhi Zhao, Lanzhou (CN); Qiyue Yang, Lanzhou (CN); Yanli Zhuang, Lanzhou (CN); Weicheng Luo, Lanzhou (CN); Hai Zhou, Lanzhou (CN); Jianjun Kang, Lanzhou (CN); Jun Du, Lanzhou (CN); Zhitao Wang, Lanzhou (CN)

(73) Assignee: Northwest Inst of Eco-Environment & Resources, CAS, Lanzhou (CN)

( * ) Notice: Subject to any disclaimer, the term of this patent is extended or adjusted under 35 U.S.C. 154(b) by 0 days.

(21) Appl. No.: 17/972,759

(22) Filed: Oct. 25, 2022

(65) Prior Publication Data
US 2023/0130523 A1    Apr. 27, 2023

(30) Foreign Application Priority Data
Oct. 26, 2021   (CN) .......................... 202111246215.8

(51) Int. Cl.
*A01G 9/02*    (2018.01)
*G01N 33/00*   (2006.01)

(52) U.S. Cl.
CPC .......... *A01G 9/02* (2013.01); *G01N 33/0098* (2013.01)

(58) Field of Classification Search
CPC ........ A01G 9/00; A01G 9/02; G01N 33/0098; G01S 13/885; G01S 7/481; Y02A 40/25; Y02A 40/10
See application file for complete search history.

(56) References Cited

FOREIGN PATENT DOCUMENTS

| CN | 211931881 U | * | 11/2020 | .............. Y02P 60/21 |
| CN | 215767187 U | * | 2/2022 | |
| CN | 114246046 A | * | 3/2022 | .............. A01D 17/00 |

OTHER PUBLICATIONS

CNIPA, Notification of a First Office Action for CN202111246215.8, dated May 11, 2022.
(Continued)

*Primary Examiner* — Ebony E Evans
(74) *Attorney, Agent, or Firm* — Zhigang Ma

(57) ABSTRACT

A rhizome-growth monitoring device of a clonal plate is provided, including a supporting frame. A first adjustment rack is fixed above a side of the supporting frame, a side end of which is movably connected to a second adjustment rack. A connection sleeve is movably connected to a bottom end of the second adjustment rack. A lifting cylinder is fixed in the connection sleeve. A camera group is fixed to the lifting cylinder through a connection plate. A rhizome growth monitoring sleeve is fixed at a bottom end of the connection plate, and includes an outer sleeve, an inner sleeve, and a radar monitoring head. The outer sleeve is fixed onto the bottom end of the connection plate. The inner sleeve is screwed to an inner side of the outer sleeve. The radar monitoring head is installed in the inner sleeve and close to a bottom surface thereof.

10 Claims, 3 Drawing Sheets

(56) References Cited

OTHER PUBLICATIONS

Northwest Institute of Eco-Environmental Resources of the Chinese Academy of Sciences (CAS) (Applicant), Reply to Notification of a First Office Action for CN202111246215.8, w/ (allowed) replacement claims, dated May 21, 2022.

CNIPA, Notification to grant patent right for invention in CN202111246215.8, dated Jul. 20, 2022.

* cited by examiner

RHIZOME-GROWTH MONITORING DEVICE OF CLONAL PLATE IN SHIFTING DUNE

TECHNICAL FIELD

The present relates to the technical field of a rhizome-growth monitoring device of a clonal plate in a dune, to a rhizome-growth monitoring device of a clonal plate in a shifting dune.

DESCRIPTION OF RELATED ART

Rhizome refers to an extended and recumbent root-like underground stem. The underground rhizome has obvious nodes and internodes, with terminal buds at a front thereof and lateral buds at a side thereof, and adventitious roots often grow downward. The adventitious roots can achieve a function of absorbing small amount of water and minerals in the soil, and the growth and extension of the terminal buds and the lateral buds can occupy a community space, and there is material transportation between roots and stems. A clonal plant occupy and utilize community resources and space through rhizome growth, and a growth speed, an extension direction and an area of the underground rhizome reflect an adaptive strategy of the cloned plant to adapt to a community environment.

At present, plant-rhizome-growth monitoring methods include the following methods.

1—Minirhi-zotron monitoring. A transparent glass plastic minirhi-zotron matched with a minirhi-zotron scanning device is embedded in a rhizome-growth direction, and monitoring of the rhizome-growth direction, a speed and a threshold are realized by regularly or irregularly placing the minirhi-zotron scanning in the minirhi-zotron and scanning a rhizome-growth state around the minirhi-zotron. However, this method has the following disadvantages. Firstly, a rhizome expansion direction cannot completely confirm to a preset direction of the minirhi-zotron, and it will deviate from the preset direction of the minirhi-zotron at a high probability, so that the minirhi-zotron scanning device cannot scan an image containing a growth trace of the monitored rhizome, and cannot obtain rhizome expansion data of the rhizome of *Psammochloa villosa*. Secondly, The minirhi-zotron is made of plastic glass, with a space left in the middle thereof for scanning and monitoring by the minirhi-zotron scanning device, and protection should be made at any time to ensure that quicksand cannot be poured into the minirhi-zotron, which will easily cause changes of micro-habitat environmental factors such as temperature and humidity around the minirhi-zotron, resulting in the phenomenon of burning roots and buds, which will affect a survival rate and a growth status of the rhizome.

2—Manual excavation and regular monitoring. Through manual excavation, sand covered on the monitored rhizome (an original expansion direction, a sand burial depth and a bud bank distribution of the rhizome of *Psammochloa villosa* should be kept during excavation) will outline an expansion direction of the monitored rhizome, and growth points of rhizome tips will be marked by iron tags, etc., and growth positions of the rhizome tips will be marked by regular or irregular manual excavation, so that the growth direction, the speed and the threshold of the rhizome can be monitored. However, this method has the following disadvantages. Firstly, the manual excavation is easy to cause damage and death of the rhizome during excavation, which affects the survival rate of the monitored rhizome. Secondly, the manual excavation will affect environmental factors around the rhizome, such as water, nutrients and microorganisms, such that the growth direction and speed of the rhizome are caused to be changed, and the related monitoring results will be wrong.

In summary, at present, information such as the direction, the speed and the threshold of the rhizome can be obtained by monitoring the growth state of the rhizome, but these methods are easy to cause damage or even death of the rhizome. Moreover, existing monitoring devices are relatively simple, the availability of available images is poor, it is required to takes time and effort to operate them and it is not easy to operate them, and a scope of application thereof is narrow, which affects the comprehensiveness of monitoring.

SUMMARY

Technical problems to be solved by the present disclosure are related to the deficiencies of the above-mentioned related art. A rhizome-growth monitoring device of a clonal plate in a shifting dune is provided, so as to solve the problems raised in the description of related art.

In order to solve the above-mentioned technical problems, a technical solution adopted in the present disclosure is as follows. The rhizome-growth monitoring device of a clonal plate in a shifting dune is provided, including a supporting frame fixed above a plant planting area; where a first adjustment rack is fixed above a side of the supporting frame, a side end of the first adjustment rack is movably connected to a second adjustment rack, and an end of the second adjustment rack is slidably connected to the supporting frame above another side of the supporting frame; where a connection sleeve is movably connected to a bottom end of the second adjustment rack, a lifting cylinder is fixed in the connection sleeve, a connection plate is fixed at a bottom end of a telescopic shaft of the lifting cylinder, a camera group is fixed at two opposite sides of the connection plate, and a rhizome-growth monitoring sleeve is fixed at a bottom end of the connection plate; and where a rhizome-growth monitoring sleeve includes an outer sleeve, an inner sleeve, and a radar monitoring head; the outer sleeve is fixed onto the bottom end of the connection plate the inner sleeve is in threaded connection with an inner side of the outer sleeve, the radar monitoring head is installed in the inner sleeve and close to a bottom surface of the inner sleeve, and a movable door is arranged at a position of a side of the inner sleeve close to the radar monitoring head.

In a preferable embodiment of the present disclosure, a vertically-arranged rod is fixed in the outer sleeve in a direction of an inner axis of the outer sleeve; where a vertically-arranged motor is fixed to a bottom end of the vertically-arranged rod, and a driving gear is fixed to a bottom end of the vertically-arranged motor; where an elongated gear is arranged in the inner sleeve, the driving gear is meshed with the elongated gear, and the vertically-arranged motor is configured to rotate to drive the driving gear to rotate, such that the inner sleeve rotates under the action of the elongated gear, and thereby the inner sleeve is screwed out.

In a preferable embodiment of the present disclosure, the outer sleeve is provided with female threads therein, the inner sleeve is provided with male threads outside, and threaded connections between the outer sleeve and the inner sleeve are achieved under the action of the male threads and the female threads.

In a preferable embodiment of the present disclosure, the movable door is movably connected to the inner sleeve through a micro hydraulic rod embedded in the inner sleeve, and a conical head is fixed at a bottom end of the inner sleeve.

In a preferable embodiment of the present disclosure, a monitoring portion of the radar monitoring head is connected to a connection seat of the radar monitoring head through a micro cylinder; and the micro cylinder is configured to drive the monitoring portion to adjust a length of a transverse section.

In a preferable embodiment of the present disclosure, the camera group includes a depth-of-field lens and a macro lens.

In a preferable embodiment of the present disclosure, the first adjustment rack includes an outer rack, a lead screw, and a thread sleeve; where the outer rack is fixed above the side of the supporting frame, the lead screw is rotatably connected to the outer rack through a bearing seat and arranged in the outer rack, and a transversely-arranged motor is fixed to the outer rack and configured to drive the lead screw to rotate through a belt ring and a belt pulley; and where the thread sleeve is in threaded connection with an outer side of the lead screw, an outer side of the thread sleeve is connected fixedly to a first connector, the first connector is slidably connected to the outer rack, and an outer end of the first connector is connected fixedly to the second adjustment rack.

In a preferable embodiment of the present disclosure, a structure of the second adjustment rack is the same as that of the first adjustment rack, a bottom end of the thread sleeve of the second adjustment rack is connected fixedly to a second connector, the second connector is slidably connected to an outer rack of the second adjustment rack, and a bottom end of the second connector is connected fixedly to the connection sleeve.

In a preferable embodiment of the present disclosure, a side end of the second adjustment rack facing away from the first adjustment rack is connected fixedly to a semi-enclosed slider, and the semi-enclosed slider is slidably connected to the supporting frame.

In a preferable embodiment of the present disclosure, the first adjustment rack and the second adjustment rack are both arranged horizontally, and are perpendicular to one another.

Compared with the related art, the present disclosure at least has the following advantages.

1. According to the present disclosure, the supporting frame is fixed above the plant planting area, and thus the plant planting area is completely surrounded by the supporting frame. The first adjustment rack is fixed above the side of the supporting frame, the second adjustment rack is fixed to the outer end of the first connector, the structure of the second adjustment rack is the same as that of the first adjustment rack, and the bottom end of the second connector is fixed to the connection sleeve, such that the first adjustment rack and the second adjustment rack can cooperate to achieve a movement of the connection sleeve above the plant planting area, so as to achieve monitoring of various positions of the plant planting area.

2. According to the present disclosure, the rhizome-growth monitoring sleeve is fixed at the bottom end of the connection plate. The rhizome-growth monitoring sleeve includes an outer sleeve, an inner sleeve, and a radar monitoring head. The outer sleeve is fixed onto the bottom end of the connection plate. The inner sleeve is in threaded connection with an inner side of the outer sleeve. The outer sleeve is provided with female threads therein, and the inner sleeve is provided with male threads outside. The threaded connections between the outer sleeve and the inner sleeve are achieved under the action of the male threads and the female threads. The vertically-arranged rod is fixed in the outer sleeve in the direction of the inner axis of the outer sleeve. The vertically-arranged motor is fixed to the bottom end of the vertically-arranged rod. The driving gear is fixed to a bottom end of the vertically-arranged motor. The elongated gear is arranged in the inner sleeve. The driving gear is meshed with the elongated gear. When the vertically-arranged motor rotates to drive the driving gear to rotate, the inner sleeve can be rotated under the action of the elongated gear, such that the inner sleeve is screwed out. During the rotation of the inner sleeve, the external male threads of the inner sleeve and the conical head can be driven to rotate, so that the inner sleeve can be easily drilled into a sand soil layer, and the rhizome-growth monitoring in the plant planting area can be achieved. When it is required to go deep into the stratum to monitor rhizome-growth of the clonal plant, the external male threads of the inner sleeve is beneficial for the device to drill into the stratum. Further, the bottom end of the inner sleeve is fixed with the conical head, which is beneficial for the device to drill into the sandy soil layer, thus improving the monitoring efficiency of going deep into the sandy soil layer.

3. According to the present disclosure, the radar monitoring head in the rhizome-growth monitoring sleeve is installed in the inner sleeve and close to the bottom surface of the inner sleeve. The radar monitoring head is an existing ground penetrating radar. When the ground penetrating radar is operated, under the control of a radar host, a pulse source generates a periodic nanosecond signal, and the periodic nanosecond signal is directly fed back to a transmitting antenna. When the signal coupled into the ground through the transmitting antenna encounters a non-uniform decent surface of a medium, such as the growing rhizome and soil on a propagation path, a reflected signal is generated. The movable door is arranged at a position of a side of the inner sleeve close to the radar monitoring head. The movable door is movably connected to the inner sleeve through a micro hydraulic rod embedded in the side of the inner sleeve close to the radar monitoring head. During the device drills into the stratum, the movable door is closed to prevent sand from entering the inner sleeve. After the device drills into a proper position, the movable door is opened, and a monitoring portion of the radar monitoring head contacts with the stratum to achieve the in-depth monitoring.

REFERENCE NUMERALS

1—supporting frame; 2—first adjustment rack; 21—outer rack; 22—lead screw; 23—thread sleeve; 24—first connector; 3—second adjustment rack; 31—second connector; 4—connection sleeve; 41—lifting cylinder; 42—connection plate; 5—camera group; 6—rhizome-growth monitoring sleeve; 61—outer sleeve; 62—inner sleeve; 63—conical head; 64—vertical-arranged rod; 65—vertically-arranged motor; 66—radar monitoring head; 67—movable door; 7—transversely-arranged motor; 8—semi-enclosed slider; 9—plant planting area.

DETAILED DESCRIPTION OF EMBODIMENTS

Technical solutions in embodiments of the present disclosure will be clearly and completely described below with reference to accompanying drawings in the embodiments of the present disclosure. It is apparent that the described embodiments are merely part of embodiments of the present disclosure, but not all of the embodiments. Based on the embodiments of the present disclosure, all other embodiments obtained by those of ordinary skill in the art without creative efforts shall fall within the protection scope of the present disclosure.

Figure 1:
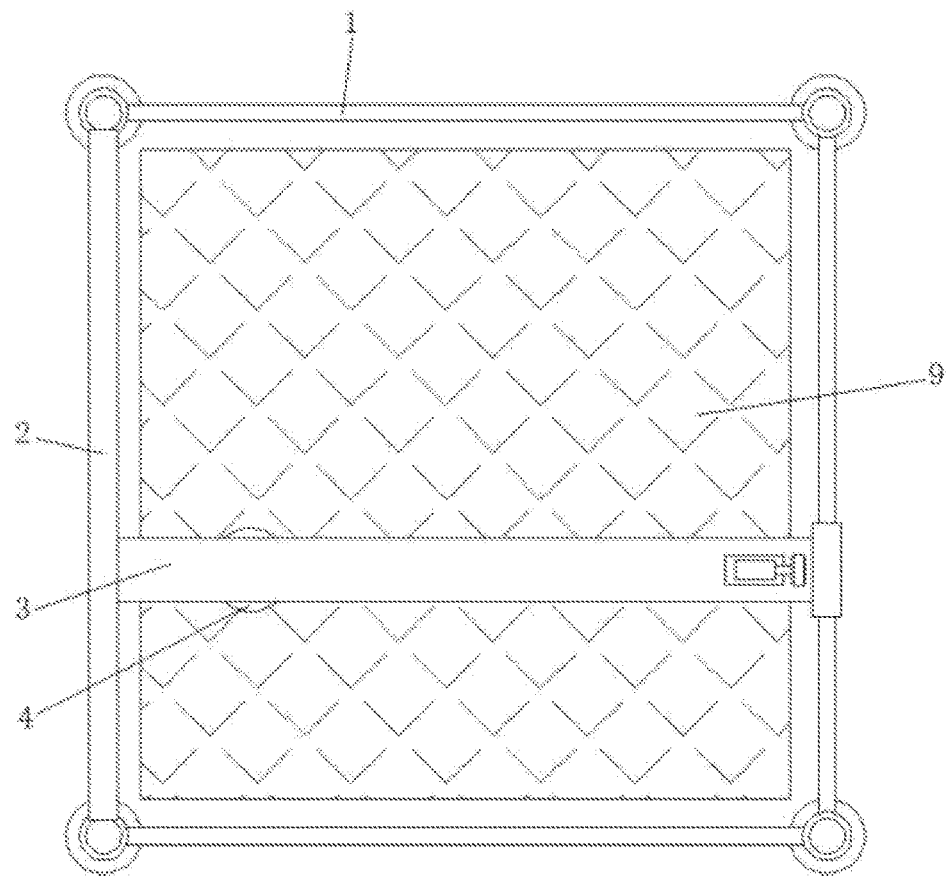
FIG. 1 illustrates a top view of an overall structure of a rhizome-growth monitoring device of a clonal plate in a shifting dune according to an embodiment of the present disclosure.
Figure 2:
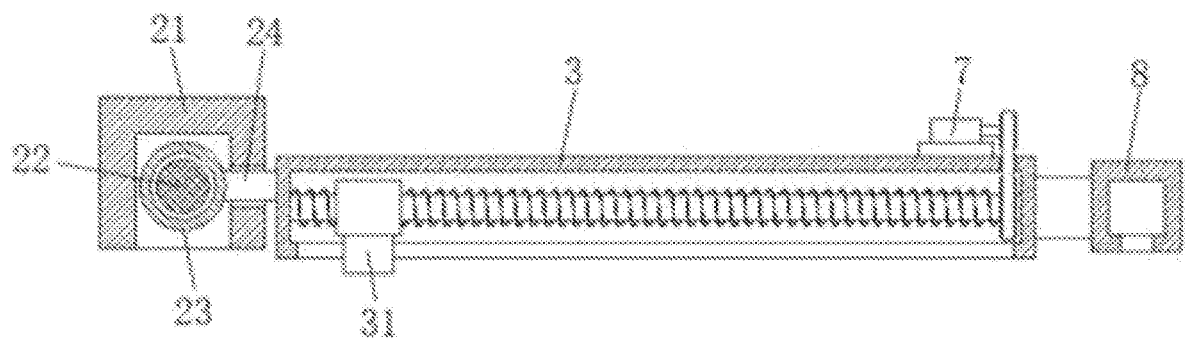
FIG. 2 illustrates a schematic view showing a connection manner between a first adjustment rack and a second adjustment rack according to an embodiment the present disclosure.
Figure 3:
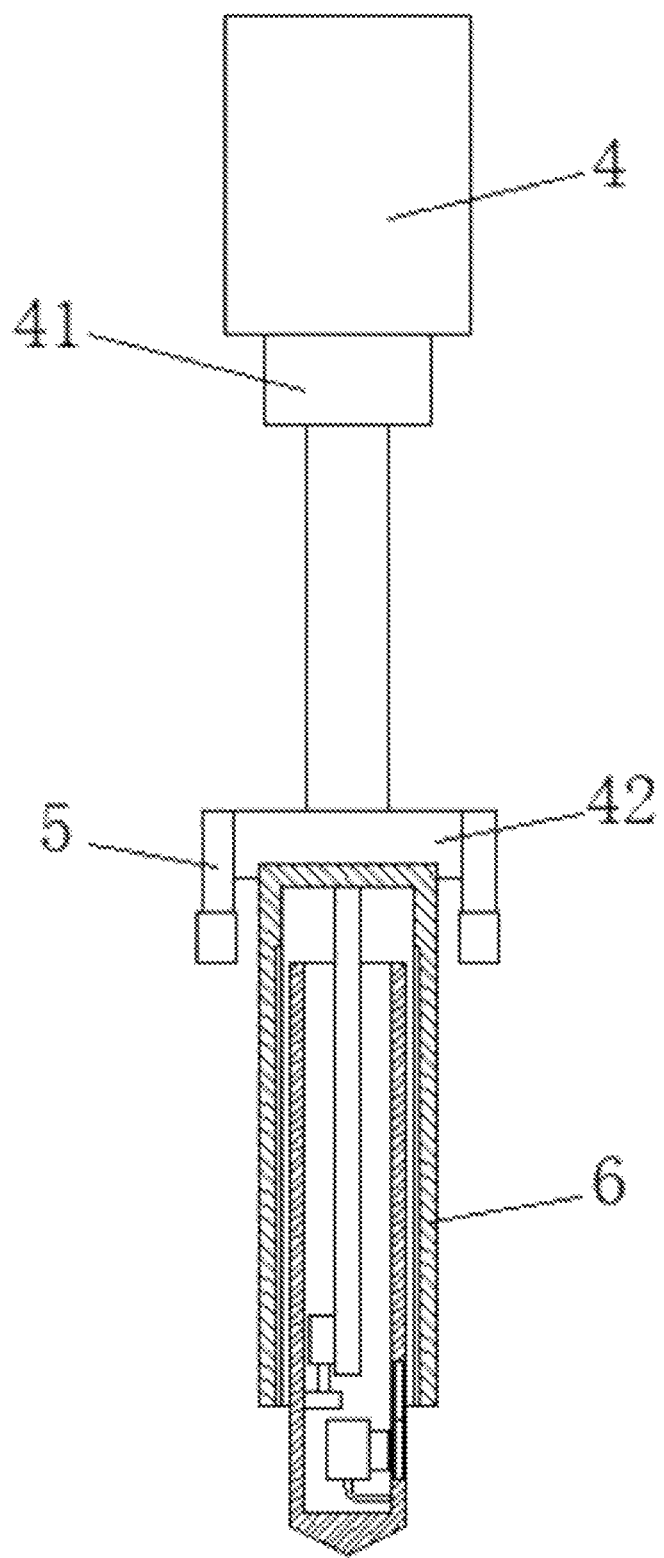
FIG. 3 illustrates a schematic view showing a connection manner between a connection sleeve and a rhizome-growth monitoring sleeve according to an embodiment the present disclosure.
Figure 4:
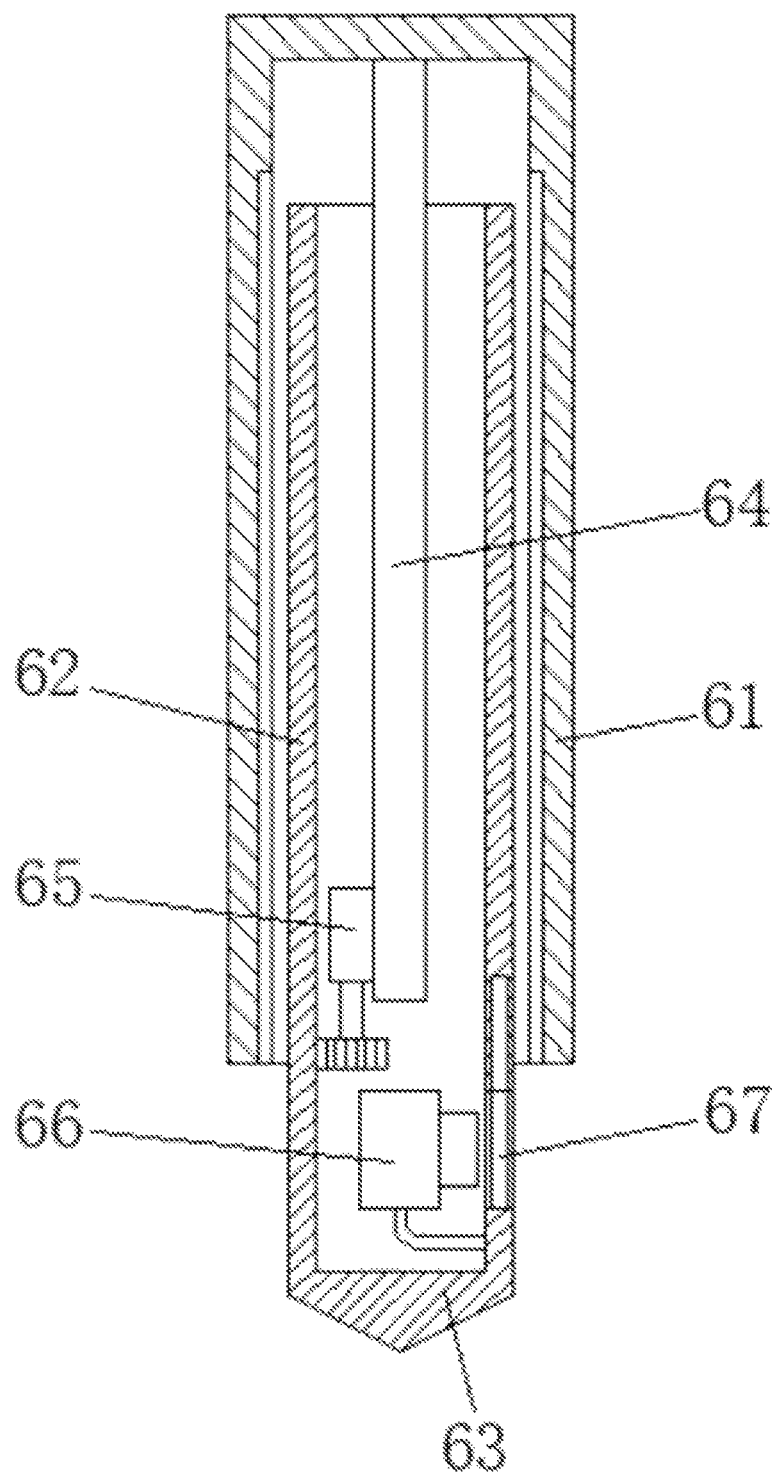
FIG. 4 illustrates a schematic showing an internal structure of the rhizome-growth monitoring sleeve according to an embodiment the present disclosure.

As shown in FIGS. 1-4, the present disclosure provides a rhizome-growth monitoring device of a clonal plate in a shifting dune, which is mainly used to monitor a direction, a speed and a threshold of rhizome growth, and includes a supporting frame 1 fixed above a plant planting area 9. The supporting frame 1 is rectangular. The plant planting area 9 is completely surrounded by the supporting frame 1, which is beneficial to complete comprehensive monitoring.

A first adjustment rack 2 is fixed above a side (i.e., an edge) of the supporting frame 1. The first adjustment rack 2 includes an outer rack 21, a lead screw 22, and a thread sleeve 23. The outer rack 21 is fixed onto the side of the supporting frame 1. The lead screw 22 is rotatably connected to the outer rack 21 through a bearing seat and arranged in the outer rack 21. A transversely-arranged motor 7 is fixed to the outer rack 21, and is configured to drive the lead screw 22 to rotate through a belt ring and a belt pulley. The thread sleeve 23 is in threaded connection with an outer side of the lead screw 22. An outer side of the thread sleeve 23 is connected fixedly to a first connector 24. The first connector 24 is slidably connected to the outer rack 21. Through a rotation of the transversely-arranged motor 7, the first connector 24 can be driven to move on the outer rack 21, and thus an adjustment of a position of the first connector 24 on the outer rack 21 can be achieved.

An outer end (opposite to an end of the first connector 24 connected to the outer side of the thread sleeve 23) of the first connector 24 is connected fixedly to a second adjustment rack 3, and a structure of the second adjustment rack 3 is the same as that of the first adjustment rack 2. A bottom end (also referred to as side) of the thread sleeve 23 of the second adjustment rack 3 is connected fixedly to a second connector 31, and the second connector 31 is slidably connected to an outer rack of the second adjustment rack 3. Similarly, through a rotation of a transversely-arranged motor connected to the second adjustment rack 3, the second connector 31 can be driven by the transversely-arranged motor to move.

A bottom end of the second connector 31 is connected fixedly to a connection sleeve 4, and the first adjustment rack 2 and the second adjustment rack 3 can cooperate to achieve a movement of the connection sleeve 4 above the plant planting area, so as to achieve monitoring of various positions of the plant planting area 9.

A side-end of the second adjustment rack 3 facing away from the first adjustment rack 2 is connected fixedly to a semi-enclosed slider 8, and the semi-enclosed slider 8 is slidably connected to the supporting frame 1. With the semi-enclosed slider 8, the second adjustment rack 3 can move smoothly, thereby improving the stability of the device during use.

The first adjustment rack 2 and the second adjustment rack 3 are both arranged horizontally and are perpendicular to one another, so as to avoid deflection during an adjustment process and protect the device from being damaged.

A lifting cylinder 41 is fixed in the connection sleeve 4, and a connection plate 42 is fixed at a bottom end of a telescopic shaft of the lifting cylinder 41. A height of the connection plate 42 from the plant planting area 9 can be adjusted by the lifting cylinder 41, thereby facilitating in-depth monitoring of rhizome-growth of the clonal plant.

A camera group 5 is fixed at two opposite sides of the connection plate 42, and the camera group 5 includes a depth-of-field lens and a macro lens. Through a cooperation of the depth-of-field lens and the macro lens of the camera group, the growth of the clonal plant on a stratum can be monitored, which can be combine with results of rhizome growth monitoring, and thus it is beneficial to the comprehensive analysis and use of later monitoring results.

A rhizome-growth monitoring sleeve 6 is fixed at a bottom end of the connection plate 42. The rhizome-growth monitoring sleeve 6 includes an outer sleeve 61, an inner sleeve 62 and a radar monitoring head 66. The outer sleeve 61 is fixed onto the bottom end of the connection plate 42. The inner sleeve 62 is in threaded connection with an inner side of the outer sleeve 61. The outer sleeve 61 is provided with female threads therein, and the inner sleeve 62 is provided with male threads outside. Threaded connections between the outer sleeve 61 and the inner sleeve 62 are achieved under the action of the male threads and the female threads. Further, when it is required the device to go deep into the stratum to perform rhizome-growth monitoring of the clonal plant, the male threads outside the inner sleeve 62 are beneficial to drilling into the stratum and it is beneficial to use the device.

The radar monitoring head 66 is installed in the inner sleeve 62 and close to a bottom surface of the inner sleeve. The radar monitoring head 66 is an existing ground penetrating radar. When the ground penetrating radar is operated, under the control of a radar host, a pulse source generates a periodic nanosecond signal, and the periodic nanosecond signal is directly fed back to a transmitting antenna. When the signal coupled into the ground through the transmitting antenna encounters a non-uniform decent surface of a medium, such as the growing rhizome and soil on a propagation path, a reflected signal is generated. After receiving an underground echo (i.e., the reflected signal), a receiving antenna located on the ground directly transmits it to a receiver. After being shaped and amplified by the receiver, the reflected signal is transmitted to the radar host through a cable, and after being processed by the radar host, the processed-reflected signal is transmitted to a microcomputer.

In the microcomputer, the processed-reflected signal is coded according to an amplitude thereof, and is displayed in a manner of a color level graph/gray level graph or a waveform stacking graph. After being processed, the graph can be used to determine specific parameters such as a depth, a distance, a size and an orientation of an underground target rhizome, so as to complete the monitoring of underground rhizome of plants.

A movable door 67 is arranged at a position of a side of the inner sleeve 62 close to the radar monitoring head 66. The movable door 67 is movably connected to the inner sleeve 62 through a micro hydraulic rod embedded in the side of the inner sleeve 62 close to the radar monitoring head 66. During the device drills into the stratum, the movable door 67 is closed to prevent sand from entering the inner sleeve 62. After the device drills into a proper position, the movable door 67 is opened, and a monitoring portion of the radar monitoring head 66 contacts with the stratum to achieve the in-depth monitoring.

The monitoring portion of the radar monitoring head 66 is connected to a connection seat of the radar monitoring head 66 through a micro cylinder. With the micro cylinder, the monitoring portion can be driven to adjust a length of a transverse section, that is to say, the monitoring portion can be driven to move laterally.

A conical head 63 is fixed at a bottom end of the inner sleeve 62, and the conical head 63 is convenient for drilling into a sandy soil layer.

A vertically-arranged rod 64 is fixed in the outer sleeve 61 in a direction of an inner axis of the outer sleeve 61. A vertically-arranged motor 65 is fixed to a bottom end of the vertically-arranged rod 64. A driving gear is fixed to a bottom end of the vertically-arranged motor 65. An elongated gear is arranged in the inner sleeve 62. The driving gear is meshed with the elongated gear. When the vertically-arranged motor 65 rotates to drive the driving gear to rotate, the inner sleeve 62 can be rotated under the action of the elongated gear, such that the inner sleeve 62 is screwed out downwardly. During the rotation of the inner sleeve 62, the external male threads of the inner sleeve 62 and the conical head 63 can be driven to rotate, so that the inner sleeve 62 can be easily drilled into the sand soil layer, and the rhizome-growth monitoring in the plant planting area 9 can be achieved.

It should be noted that, relational terms herein such as first and second are merely used to distinguish one entity or operation from another entity or operation, and do not necessarily require or imply any such actual relationship or sequence between these entities or operations. Moreover, the term "includes", "comprises" or any other variation thereof is intended to cover non-exclusive inclusion, so that a process, a method, an article or a device that includes a series of elements not only includes those elements, but also includes other elements not explicitly listed, or also includes elements inherent to such process, method, article or device.

Although the embodiments of the present disclosure have been shown and described, it will be understood by those skilled in the art that many changes, modifications, substitutions and variations can be made to these embodiments without departing from the principle and spirit of the present disclosure, and the scope of the present disclosure is defined by the appended claims and their equivalents.

What is claimed is:

1. A rhizome-growth monitoring device of a clonal plate in a shifting dune, comprising a supporting frame (1) fixed above a plant planting area (9);

wherein a first adjustment rack (2) is fixed above a side of the supporting frame (1), a side end of the first adjustment rack (2) is movably connected to a second adjustment rack (3), and an end of the second adjustment rack (3) is slidably connected to the supporting frame (1) above another side of the supporting frame (1);

wherein a connection sleeve (4) is movably connected to a bottom end of the second adjustment rack (3), a lifting cylinder (41) is fixed in the connection sleeve (4), a connection plate (42) is fixed at a bottom end of a telescopic shaft of the lifting cylinder (41), a camera group (5) is fixed at two opposite sides of the connection plate (42), and a rhizome-growth monitoring sleeve (6) is fixed at a bottom end of the connection plate (42); and wherein the rhizome-growth monitoring sleeve (6) comprises an outer sleeve (61), an inner sleeve (62), and a radar monitoring head (66); and the outer sleeve (61) is fixed onto the bottom end of the connection plate (42), the inner sleeve (62) is in threaded connection with the outer sleeve (61), the radar monitoring head (66) is installed in the inner sleeve (62) and close to a bottom surface of the inner sleeve (62), and a movable door (67) is arranged at a position of a side of the inner sleeve (62) close to the radar monitoring head (66).

2. The rhizome-growth monitoring device of the clonal plate in the shifting dune according to claim 1, wherein a vertically-arranged rod (64) is fixed in the outer sleeve (61) in a direction of an inner axis of the outer sleeve (61);

wherein a vertically-arranged motor (65) is fixed to a bottom end of the vertically-arranged rod (64), and a driving gear is fixed to a bottom end of the vertically-arranged motor (65);

wherein an elongated gear is arranged in the inner sleeve (62), the driving gear is meshed with the elongated gear, and the vertically-arranged motor (65) is configured to rotate to drive the driving gear to rotate, such that the inner sleeve (62) rotates under the action of the elongated gear, and thereby the inner sleeve (62) is screwed out.

3. The rhizome-growth monitoring device of the clonal plate in the shifting dune according to claim 1, wherein the outer sleeve (61) is provided with female threads on an inner surface thereof, the inner sleeve (62) is provided with male threads on an outer surface thereof, and threaded connections between the outer sleeve (61) and the inner sleeve (62) are achieved under the action of the male threads and the female threads.

4. The rhizome-growth monitoring device of the clonal plate in the shifting dune according to claim 1, wherein the movable door (67) is movably connected to the inner sleeve (62) through a micro hydraulic rod embedded in the inner sleeve (62), and a conical head (63) is fixed at a bottom end of the inner sleeve (62).

5. The rhizome-growth monitoring device of the clonal plate in the shifting dune according to claim 1, wherein a monitoring portion of the radar monitoring head (66) is connected to a connection seat of the radar monitoring head (66) through a micro cylinder; and the micro cylinder is configured to drive the monitoring portion to adjust a length of a transverse section.

6. The rhizome-growth monitoring device of the clonal plate in the shifting dune according to claim 1, wherein the camera group (5) comprises a depth-of-field lens and a macro lens.

7. The rhizome-growth monitoring device of the clonal plate in the shifting dune according to claim 1, wherein the first adjustment rack (2) comprises an outer rack (21), a lead screw (22), and a thread sleeve (23);

wherein the outer rack (21) is fixed above the side of the supporting frame (1), the lead screw (22) is rotatably connected to the outer rack (21) through a bearing seat and arranged in the outer rack (21), and a transversely-arranged motor (7) is fixed to the outer rack (21) and configured to drive the lead screw (22) to rotate through a belt ring and a belt pulley; and wherein the thread sleeve (23) is in threaded connection with an outer side of the lead screw (22), an outer side of the thread sleeve (23) is connected fixedly to a first connector (24), the first connector (24) is slidably connected to the outer rack (21), and an outer end of the first connector (24) is connected fixedly to the second adjustment rack (3).

8. The rhizome-growth monitoring device of the clonal plate in the shifting dune according to claim 7, wherein a structure of the second adjustment rack (3) is the same as that of the first adjustment rack (2), a bottom end of the thread sleeve (23) of the second adjustment rack (3) is connected fixedly to a second connector (31), the second connector (31) is slidably connected to an outer rack of the second adjustment rack, and a bottom end of the second connector (31) is connected fixedly to the connection sleeve (4).

9. The rhizome-growth monitoring device of the clonal plate in the shifting dune according to claim 1, wherein a side end of the second adjustment rack (3) facing away from the first adjustment rack (2) is connected fixedly to a semi-enclosed slider (8), and the semi-enclosed slider (8) is slidably connected to the supporting frame (1).

10. The rhizome-growth monitoring device of the clonal plate in the shifting dune according to claim 1, wherein the first adjustment rack (2) and the second adjustment rack (3) are both arranged horizontally, and are perpendicular to one another.

\* \* \* \* \*